United States Patent [19]

Ito et al.

[11] Patent Number: 5,332,504
[45] Date of Patent: Jul. 26, 1994

[54] PH-ZONE-REFINING COUNTERCURRENT CHROMATOGRAPHY

[75] Inventors: Yoichiro Ito, Bethesda; Adrian Weisz, Silver Spring, both of Md.

[73] Assignee: The United States of America as represented by the Department of Health and Human Services, Washington, D.C.

[21] Appl. No.: 26,939

[22] Filed: Mar. 5, 1993

[51] Int. Cl.$^5$ ............................................. B01D 15/08
[52] U.S. Cl. .................................. 210/635; 210/657; 210/198.2
[58] Field of Search ............... 210/635, 656, 657, 659, 210/96.1, 101, 198.2, 658, 198.3; 436/161; 95/82; 96/101

[56] References Cited

U.S. PATENT DOCUMENTS

| | | | |
|---|---|---|---|
| 5,114,589 | 5/1992 | Shibusawa | 210/657 |
| 5,217,608 | 6/1993 | Conway | 210/657 |
| 5,273,656 | 12/1993 | Anderson | 210/657 |

OTHER PUBLICATIONS

Yoichiro Ito, "Cross-Axis Synchronous Flow-Through Coil Planet Centrifuge Free of Rotary Seals for Preparative Countercurrent Chromatography. Part 1. Apparatus and Analysis of Acceleration", in: Separation Science and Technology 22(8-10), 1972, pp. 1971-1987.

Y. Ito, "High-speed countercurrent chromatography", reprinted from: Nature, vol. 326, No. 6111, Mar. 26, 1987, pp. 419-420.

Yoichiro Ito, "Cross-Axis Synchronous Flow-Through Coil Planet Centrifuge Free of Rotary Seals for Preparative Countercurrent Chromatography. Part II. Studies on Phase Distribution and Partition Efficiency in Coaxial Coils", In: Separation Science and Technology 22(8-10), 1987, pp. 1989-2009.

Yoichiro Ito and Tian-You Zhang, "Cross-Axis Synchronous Flow-Through Coil Planet Centrifuge For Large-Scale Preparative Counter-Current Chromatography", in: Journal of Chromatography, 449 (1988), pp. 135-151.

Yoichiro Ito and Tian-You Zhang, "Cross-Axis Synchronous Flow-Through Coil Planet Centrifuge For Large-Scale Preparative Counter-Current Chromatography, II. Studies on Partition Efficiency in Short Coils and Preparative Separations with Multilayer Coils" in: Journal of Chromatography, 449 (1988), pp. 153-164.

Yoichiro Ito and Tian-You Zhang, "Cross-Axis Synchronous Flow-Through Coil Planet Centrifuge For (List continued on next page.)

*Primary Examiner*—Ernest G. Therkorn
*Attorney, Agent, or Firm*—Townsend and Townsend Khourie and Crew

[57] ABSTRACT

It has now been discovered that acidic or basic compounds may be purified using a new countercurrent chromatography technique. This technique utilizes two immiscible solvent phases, one being acidic and one being basic. The solutes partition between the phases and elute in contiguous, well-resolved, rectangularly shaped peaks in order of their partition coefficients. The fractions within any single peak have a substantially constant concentration. In addition to differing partition coefficients, the peaks also differ in pH, successively increasing in the case of a basic mobile phase and successively decreasing in the case of an acidic mobile phase. For this reason, the technique may be referred to as "pH-zone-refining countercurrent chromatography."

The method of this invention provides certain advantages over previously known countercurrent chromatography techniques. First, the method permits one to load a sample as a suspension into the separation column. Additionally, the minimal degree of elution peak overlap permits one to separate mixtures of greater volume than before in any given column without loss of resolution. Thus, columns which are otherwise recommended for separations of mixtures up to a certain maximum size can be used in the method of this invention for separating mixtures up to ten times that size or greater.

16 Claims, 13 Drawing Sheets

OTHER PUBLICATIONS

Large-Scale Preparative Counter-Current Chromatography. III. Performance of Large-Bore Coils in Slow Planetary Motion", in: Journal of Chromatography, 449 (1988), pp. 152–162.

Walter D. Conway, *Countercurrent Chromatography*, VCH Publishers, Inc., New York 1990, pp. 1–115.

Hans J. Cahnmann, et al., "Synthesis and Characterization of N-bromoacecyl-3,3',5-triiodo-L-thyronine", in: Journal of Chromatography, 538 (1991), pp. 165–175.

Yoichiro Ito, et al., "Improved high-speed counter-current chromatograph with three multilayer coils connected in series" IV. Evaluation of preparative capability with large multilayer cells, in: Journal of Chromatography, 538 (1991), pp. 81–85.

Yoichiro Ito, et al., "Cross-axis synchronous flow-through coil planet centrifuge (Type XLL). I. Design of the apparatus and studies on retention of stationary phase", in: Journal of Chromatography, 538 (1991) pp. 59–66.

Adrian Weisz, et al., "Complementary use of counter-current chromatography and preparative reversed-phase high-performance liquid chromatography in the separation of a synthetic mixture of brominated tetrachlorofluoresceins", in: Journal of Chromatography, 607 (1992), pp. 47–53.

Yoichiro Ito, "High-Speed Countercurrent Chromatography", in: CRC Critical Reviews in Analytical Chemistry, vol. 17, Issue 1 pp. 65–143 (1986).

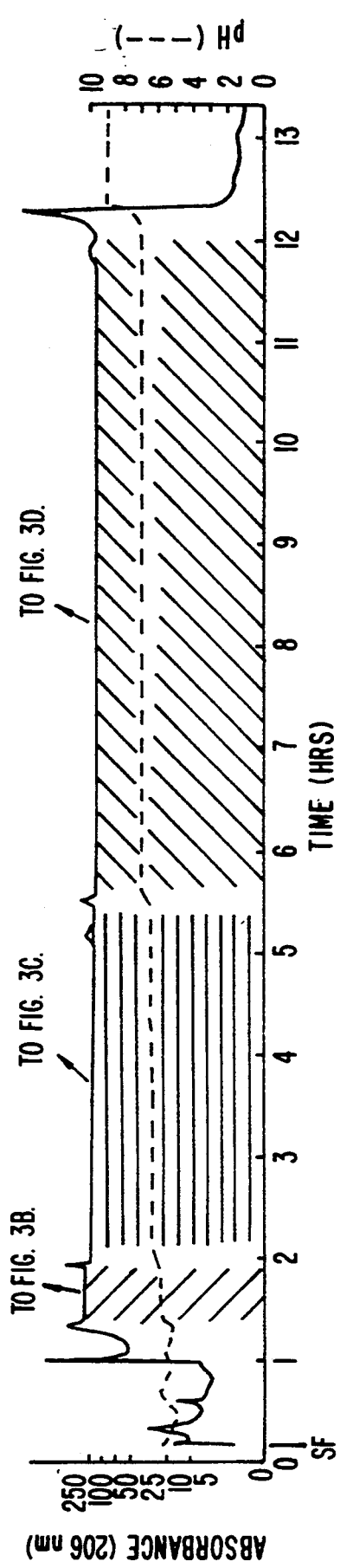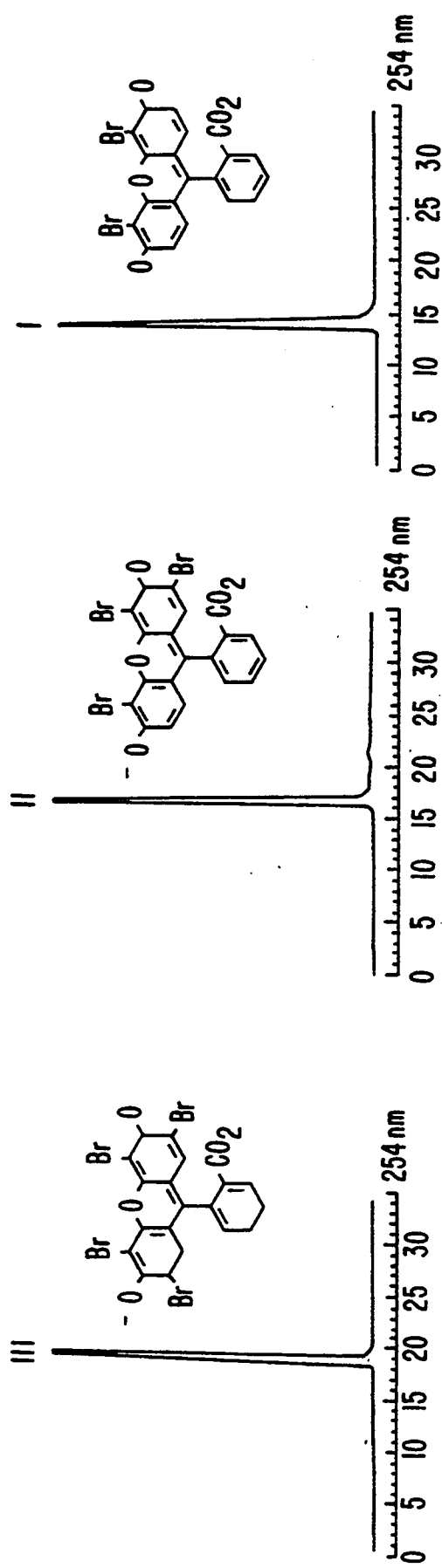
FIG. 3A.
FIG. 3B.
FIG. 3C.
FIG. 3D.

fr. 78-80, 24 mg fr. 102-103, 3 mg fr. 105-109, 5 mg fr. 116-168, 208 mg fr. 92-97, 0.6 mg
$C_{19}H_7Cl_3O_3$

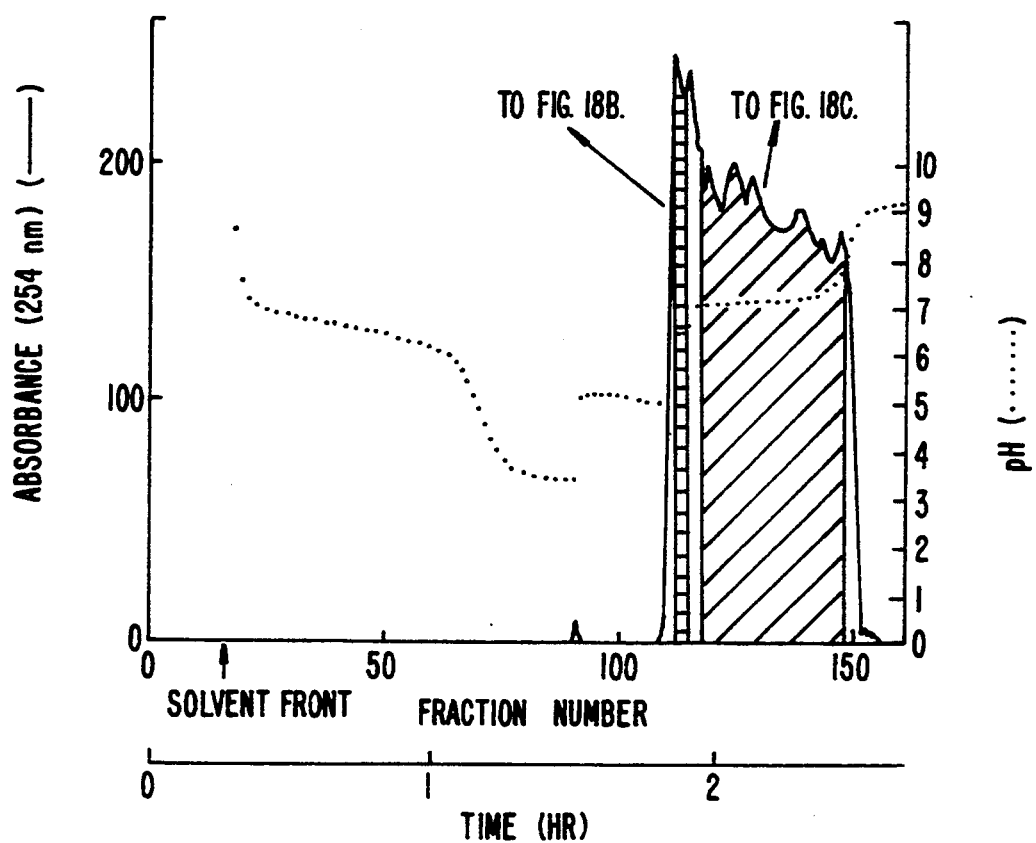
FIG. 18A.
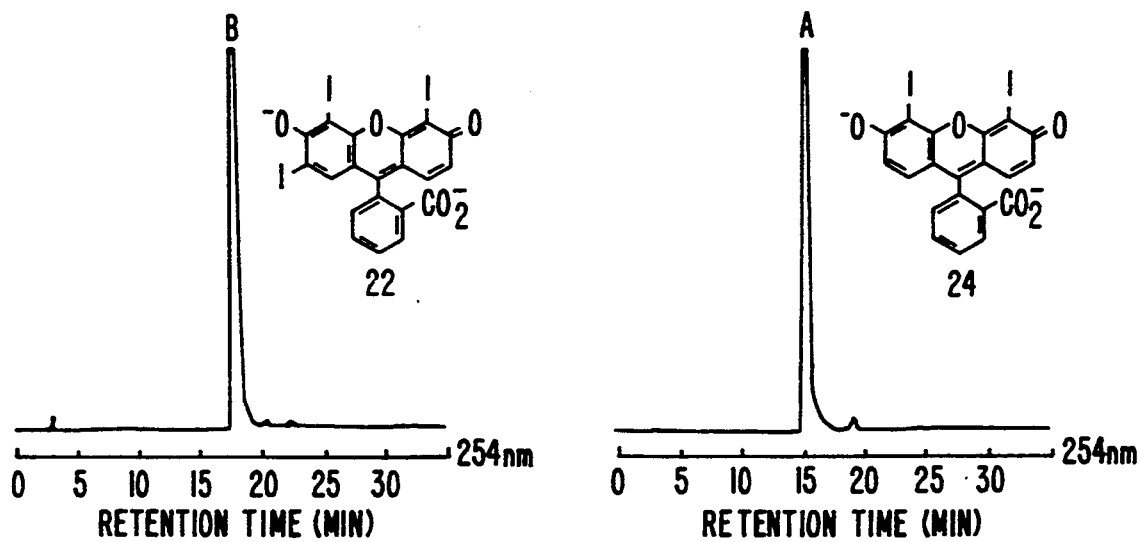
FIG. 18B.
FIG. 18C.

PH-ZONE-REFINING COUNTERCURRENT CHROMATOGRAPHY

This invention lies in the field of liquid-liquid partition chromatography, and in particular in the separation of acid or basic solutes from a mixture of such solutes using chromatographic techniques.

BACKGROUND OF THE INVENTION

Countercurrent chromatography (CCC) is a form of liquid-liquid partition chromatography which relies on the continuous contact between two immiscible solvents, one of which is mobile relative to the other, in a flow-through tubular column, free of any solid support matrix. The retention time of a solute in the phase contact region of the system is determined by the volume ratio of the solvents, the partition coefficient of the solute between the solvents, and the degree of contact between the solvents. Like other forms of liquid-liquid partition chromatography, one of the solvents serves as a carrier, drawing the solutes from the other solvent and carrying the solutes out of the column in the order of elution. This carrier solvent is thus referred to as the mobile phase, while the other solvent is referred to as the stationary phase, even though it is not strictly stationary in many applications of the method. Solvent mixing, retention of the stationary phase in the column, and solute partitioning all take place in the column by the aid of a suitable acceleration field established by gravity, centrifugal force or both, and the configuration of the column.

Most equipment used for CCC separations involves a coil of column tubing, a portion of which is filled with the stationary phase while the mobile phase is passed through it. By varying the length and diameter of the tubing, CCC has been used for both analytical and preparative separations.

The flow rate of the mobile phase may be varied by varying the field imposed on the column. Units which operate in the presence of a gravitational field only are restricted to slow flow rates, with the resulting separations typically requiring 1 to 3 days, to avoid displacing the stationary phase. A unit which operates in the presence of a centrifugal acceleration field of 40 g or more allows faster flow rates and permits separation times of only a few hours.

Separations by CCC may be performed using any immiscible pair of solvents, provided that the solvents differ in density to at least a slight degree. Both normal-phase and reverse-phase separations may be performed, with the more polar solvent as the stationary phase for normal-phase separations, and the less polar solvent as the stationary phase for reverse-phase separations.

The operational aspects of CCC are similar to the more conventional liquid-liquid chromatography (LLC). Typically, after the immiscible solvent phases are equilibrated relative to one another, the column is filled with the stationary phase. The sample is then injected into the column and elution with the mobile phase is begun. The centrifuge is then started and the eluting fractions are collected. Initially, the fractions are composed of the stationary phase which is displaced from the column. However, once hydrodynamic equilibrium between the phases is achieved, only small portions of the stationary phase will co-elute with the mobile phase. The collected fractions are monitored by any of a variety of means including spectroscopic methods and thin-layer chromatography.

Countercurrent chromatographic theory, as well as apparatus for performing the method, are described by Ito, Y., in "Principle and Instrumentation of Countercurrent Chromatography," in *Countercurrent Chromatography: Theory and Practice* Mandava, N. B., and Ito, Y., eds., pp. 79–442 (Marcel Dekker, N.Y., 1988) and by Conway, W. D., in *Countercurrent Chromatography: Apparatus, Theory and Applications* (VCH, N.Y., 1990). Most countercurrent chromatographs use a column which is formed into a helical coil. This coil is in turn mounted onto a column holder in various configurations relative to the means for rotating it and relative to the acceleration field that acts on it.

Each column and each type of rotation produce different types of mixing between the solvent phases and are particularly suited for specific separations. However, certain disadvantages to CCC exist.

One disadvantage associated with CCC is the increased peak width associated with increased retention time of the solute. This increased peak width makes detection of the solute more difficult, and requires a larger volume of eluate to be collected and processed in order to obtain a maximum yield of solute. This disadvantage is particularly acute when preparative separations are desired. Nevertheless, increased retention time is desirable in order to avoid coeluting impurities with the solute. Commonly-owned, United States patent application Ser. No. 07/946,613, filed Sep. 18, 1992, abandoned, discloses a method for obtaining sharp elution peaks in analytical or semi-preparative CCC without decreasing the retention time of the solute, by adding a peak sharpening agent to either the stationary phase or the sample mixture. When acidic compounds are to be separated, the peak sharpening agent is an acid. When basic solutes are to be separated, the peak sharpening agent is a base.

SUMMARY OF THE INVENTION

It has now been discovered that an unusually efficient separation of mixtures of acids or bases is achieved by a unique modification of the techniques of countercurrent chromatography. According to this modification, the two immiscible liquid solutions which are to serve as the stationary and mobile phases, respectively, are modified prior to the performance of the separation by rendering one of the phases acid and the other basic. Separation of a mixture of acids is then performed in a system in which the acidified solution serves as the stationary phase and the basified solution as the mobile phase. Conversely, separation of a mixture of bases is performed in a system in which the basified solution serves as the stationary phase and the acidified solution as the mobile phase. Individual acid or basic solutes separated by this method elute in contiguous, well-resolved, rectangularly shaped peaks, the solutes eluting in order of their partition coefficients (related to their $pK_a$ values and hydrophobicity) and the fractions within any single peak being of substantially constant concentration. In addition to differing partition coefficients, the combined fractions within each peak also differ in pH, successively increasing in the case of a basic mobile phase and successively decreasing in the case of an acidic mobile phase. For this reason, the technique may be referred to for convenience as "pH-zone-refining countercurrent chromatography."

The method of this invention entails certain advantages over previously known counter-current chromatography techniques. First, the method permits one to load the sample as a suspension into the separation column. Thus, mixtures of compounds that are only partially soluble in the solvent system can be separated efficiently. In addition, the lack or small degree of elution peak overlap permits one to separate mixtures of greater volume than before in any given column without loss of resolution. For example, columns which are otherwise recommended for separations of mixtures of a certain maximum size can be used in the method of this invention for separating mixtures up to ten times that size or greater. Likewise, mixtures containing higher concentrations of the acid or basic solutes can be separated with no loss in resolution. As the concentration of solute increases, the separation simply produces a wider plateau for each solute.

Additional advantages and features of the invention and its preferred embodiments will be apparent from the description which follows.

BRIEF DESCRIPTION OF THE DRAWINGS

FIG. 3 shows the separation of 5 g of D&C Orange No. 5 by pH-zone-refining CCC. FIG. 3A shows the trace from the collected fractions following pH-zone-refining CCC. FIGS. 3B, 3C and 3D show reverse phase high performance liquid chromatography (RP-HPLC) traces of the combined fractions (see hatched areas) corresponding to the separated components of D&C Orange No. 5 (see Example 3). These components are the brominated hydroxyxanthenes labelled as compounds III, II, and I.

FIG. 6 shows the separation of 5 g of D&C Red No. 22 by pH-zone-refining CCC.

FIG. 12 shows the separation of 3 g of D&C Red No. 28 by pH-zone-refining CCC.

FIG. 14 shows the separation of 6 g of D&C Red No. 28 by pH-zone-refining CCC.

FIG. 16 shows the separation of 3 g of FD&C Red No. 3 by pH-zone-refining CCC.

FIG. 18 shows the separation of a 350 mg portion of D&C Orange No. 10 by pH-zone-refining CCC. FIG. 18A shows the trace from the collected fractions following pH-zone-refining CCC. FIGS. 18B and 18C show RP-HPLC chromatograms of the combined fractions corresponding to the separated components of D&C Orange No. 10.

DESCRIPTION OF THE PREFERRED EMBODIMENT

Figure 1:
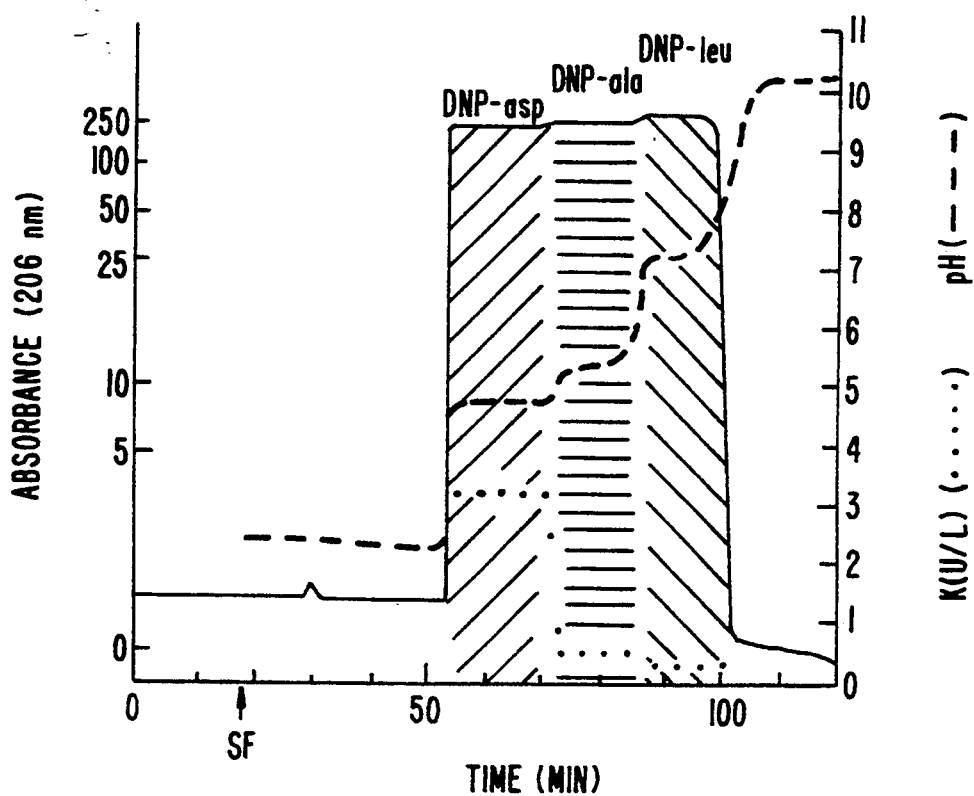
FIG. 1 is a chromatographic trace which shows the model separations of a mixture of three 2,4-dinitrophenyl(DNP)-amino acids (DNP-L-aspartic acid, DNP-L-alanine, and DNP-L-leucine (100 mg each)) by pH-zone-refining CCC (as described in Example 1).

As used herein, the term "acidic compound" means an organic compound having an acidic functionality such as a carboxylic acid, phosphoric acid, phosphonic acid, phosphinic acid, sulfonic acid, sulfinic acid, phenol or the like. These acidic compounds may also be termed "retaining acids."

As used herein, the term "basic compound" means an organic compound having a basic functionality such as an amine, imine, amidine, guanidine or the like. These basic compounds may also be termed "retaining bases."

As used herein, the term "separating" means to increase the amount of one component relative to the amounts of other components in a sample mixture. The mixture produced upon "separating" one component will be substantially free from the other components in the sample mixture, but may contain added quantities of solvents.

As used herein, the phrase "immiscible liquid phases" refers to liquids which may be partially miscible, but which separate into two phases having a liquid interface on standing. Typically, the two phases will comprise an organic phase and an aqueous phase. Suitable organic solvents include diethyl ether, hexane, ethyl acetate, methanol, methyl t-butyl ether, and acetonitrile.

As used herein, the term "identifying" means determining by spectroscopic means such as UV detection, refractive index detection, mass spectroscopy, and IR detection whether the desired compound is present in a particular sample or eluted fraction. Compounds may also be "identified" by a comparison of their elution times using HPLC.

The method of the present invention utilizes a countercurrent chromatographic centrifuge which may be any of the centrifuges generally used in other modes of countercurrent chromatography. A variety of these centrifuges have been described by Ito, Y., in "Principle and Instrumentation of Countercurrent Chromatography," in *Countercurrent Chromatography: Theory and Practice* Mandava, N.B., and Ito, Y., eds., pp. 79–442 (Marcel Dekker, New York, 1988) and by Conway, W.D., in *Countercurrent Chromatography: Apparatus, Theory and Applications* (VCH, New York, 1990).

Countercurrent chromatography utilizes the hydrodynamic behavior of two immiscible solvent phases mixing in a column to effect the separation of a solute from other components in a sample.

Any mixture of solvents which forms two phases on standing may be used. The phases may each be independently composed of organic solutions or aqueous solutions. In a preferred embodiment, one phase is composed of one or more organic solvents and the other phase is substantially aqueous. When chromatography is conducted with the aid of a centrifuge, preferred solvents are those which form two phases having a difference in density of at least 0.05 g/mL. The phases may be equilibrated relative to one another either prior to or during chromatography. Additionally, the phases may be equilibrated prior to acidifying or basifying the separate phases. When a basic aqueous phase is used as a mobile phase for separation of acidic solutes, the phases may be equilibrated after the aqueous phase is made basic. Similarly, when an acidic aqueous phase is used as a mobile phase for the separation of basic solutes, the phases may be equilibrated after the aqueous phase is made acidic. In a preferred embodiment, the phases are equilibrated in their neutral form by shaking them together and then allowing them to separate prior to charging the column with the stationary phase. When the phases are equilibrated in their neutral form, the stationary phase may be acidified (for separation of acidic solutes) or basified (for separation of basic solutes) prior to charging the chromatography column. Alternatively, the sample solution may be acidified with a retaining acid or basified with a retaining base.

The degree of acidity and basicity of the two phases is not critical. In most applications, best results will be achieved by using an acidic phase with a pH below about 4 and preferably below about 3. Similarly, the basic phase will in most cases have a pH above about 8 and preferably above about 9. The use of a more basic mobile phase will result in shorter elution times for acidic compounds. Similarly, a more acidic mobile phase will reduce the elution times of basic samples.

The suitability of a desired two-phase solvent system can be determined by comparing the partition coefficient of the sample in both acidic environments, $K_a(U/L)$, and in basic environments, $K_b(U/L)$. To obtain a value for $K_a(U/L)$, the sample and retaining acid are added to a mixture of aliquots from the two phases (to give a concentration of approximately 10 mM). The phases are separated, diluted with an organic solvent such as methanol, and the absorbance of each phase is measured at an appropriate wavelength. The partition coefficient, $K_a(U/L)$, is obtained by dividing the absorbance of the upper phase by that of the lower phase. Similarly, to obtain a value for $K_b(U/L)$, the sample and a small amount of aqueous ammonia (28%) is added to a mixture of aliquots from the two phases. The mixture is equilibrated and the partition coefficient, $K_b(U/L)$ is measured as previously described. If $K_a(U/L) >> 1 >> K_b(U/L)$, the solvent system can be effectively used to separate an acidic sample. When $K_a(U/L)$ is 2 or less, the above test should be repeated with a more hydrophobic solvent system. When $K_b(U/L)$ is greater than 0.5, a more polar solvent system should be tested.

The sample mixture may be prepared by partitioning the sample between amounts of the two phases prior to injection into the column or the sample may be injected without added solvents. Additionally, the sample need not be completely soluble in the two solvent phases but may be injected into the column as a suspension. In a preferred embodiment, the sample mixture is prepared by solubilizing the sample in small portions of each of the two solvent phases. In the case where the stationary phase is left neutral, the retaining acid or base is added to the sample mixture.

The motions which are applied to a CCC column are best described as corresponding to a solar system. In particular, a coiled column may undergo rotation about one or more axes. Solar coaxial motion is found when the coiled column is rotated about the axis of the coil. When the coil is mounted with its axis parallel and offset from a second axis, and the column is rotated only about the second axis, the rotation is termed solar satellite or solar eccentric motion. Planetary motion is provided when rotation occurs about two axes. When a coiled column is rotated about its own axis and also rotated about a second parallel axis, the motion is termed planetary coaxial motion. When a coiled column is rotated about a first external axis parallel to the axis of the coiled column, and the first external axis is simultaneously revolving about a second external parallel axis, the motion is termed planetary satellite or planetary eccentric motion.

In addition to configurations having parallel axes, there are also configurations in which the column axis is inclined or skewed relative to the external axes. Another type of planetary motion results when the two axes about which rotation occurs are orthogonal to one another. Methods utilizing this type of configuration are termed cross-axis CCC.

The columns employed in CCC are equally diverse. The majority are helical, but may vary in the material of fabrication, length, width, pitch of its winding, and mounting onto a column holder. Modern columns are typically constructed of polytetrafluoroethylene tubing which is capable of maintaining its shape and integrity while being exposed to a strong acceleration field. The inside diameter of the tubing is typically between 0.75 and 3 mm. While a single-layer coil may involve only a few meters of tubing, a multi-layer coil might contain more than 100 m of the tubing. Columns to be used for analytical purposes typically have an inside diameter which is more narrow and a length which is longer than a column used for preparative purposes. Additionally, helical columns may be either right-handed or left-handed. The handedness of the coils are determined by the direction in which the coils are wound onto a spool-shaped column holder. The helical column may be either a single layer or multilayer coil. For another column shape, the tubing may be wound onto a flexible core which is in turn coiled onto the column holder to produce a toroidal coil. Yet another type of column is a single layer spiral in which the tubing is wound in one layer onto a core and upon itself. The columns are further equipped with flow tubes which provide for the introduction of sample and mobile phases using an external pump. The tubes further allow the eluate to be collected using an automated fraction collector.

The present invention can be used with any of the columns and motions employed for CCC. The preferred apparatus is a high-speed countercurrent chromatographic centrifuge having a multilayer-coil separation column. The preferred motion is planetary motion (either coaxial or eccentric). Particularly preferred is synchronous planetary motion in which the number of revolutions about each of the two axes of rotation is the same within a particular period of time. The synchronous planetary motion provided by the centrifuge performs two functions. First, the synchronous rotation of the column holder constantly unwinds the twist of the flow tubes caused by revolution. This permits continuous elution through the rotating coil without the use of a conventional rotary seal device, which can be a potential source of leakage and contamination of collected fractions. Additionally, when the coiled column is coaxially mounted about the coil holder, the planetary motion of the holder unilaterally distributes two solvent phases in the column in such a way that one phase occupies the head side, and the other phase occupies the tail side of the coil. This head-tail relationship refers to the Archimedean screw force acting on the rotating coil, where all objects of different density are driven from the tail portion of the coil toward the head of the coil. This hydrodynamic phenomenon can be utilized for performing CCC in two ways. The coil can be entirely filled with a first liquid phase and eluted with the second liquid phase from the tail toward the head. Alternatively, the coil can be filled with the second liquid phase followed by elution with the first liquid phase from the head toward the tail. In either case the hydrodynamic phenomenon facilitates rapid movement of the mobile phase through the stationary phase, yielding extremely high retention of the stationary phase in the coil.

In one group of embodiments, the present inventive method is used to separate an acidic compound from other compounds in a sample mixture. Two immiscible solvent phases are equilibrated relative to one another to yield a two-phase mixture. A countercurrent chromatographic centrifuge column is then charged with a first liquid phase of the mixture. The first liquid phase is made acidic, and the sample mixture containing the acidic compound to be separated is introduced into the column. The centrifuge is started and the second liquid phase, which has previously been made basic, is passed through the column. Fractions containing the various components of the mixture are eluted, collected and identified.

The liquid phases are each independently an organic phase or an aqueous phase. In a preferred embodiment, the first liquid phase is an organic phase and the second liquid phase is an aqueous phase. In a further preferred embodiment, the first liquid phase is made acidic with an organic acid which is either acetic acid, trifluoroacetic acid, propionic acid or butanoic acid. In a still further preferred embodiment, the first liquid phase is made acidic with trifluoroacetic acid.

In other preferred embodiments, the method of the present invention can be carried out on a preparative scale, using 0.01 to 100 g of the mixture which is to be separated. Additionally, the mixture to be chromatographed may be either a homogeneous solution or a suspension.

In another group of embodiments, the present inventive method is used for separating a quantity of a basic compound in a sample mixture. In these embodiments, two immiscible liquid phases are equilibrated relative to one another, then separated. A countercurrent chromatographic centrifuge column is charged with a first liquid phase which is made basic either prior to or following its introduction into the column. The mixture containing a quantity of a basic compound to be separated is then introduced into the column. The centrifuge is started and the second liquid phase, which has previously been made acidic, is passed through the column. Fractions containing the various components of the mixture are eluted, collected and identified.

As above, the liquid phases are each independently an organic phase or an aqueous phase. In a preferred embodiment, the first liquid phase is an organic phase and the second liquid phase is an aqueous phase. In another preferred embodiment, pH-zone-refining countercurrent chromatography can be conducted on a preparative scale using 0.01 to 100 grams of the mixture containing the basic compound which is to be separated. In a still further preferred embodiment, the method can be used for separating a quantity of a basic compound in a suspension.

The following examples are offered by way of illustration and are not meant to limit the scope of the invention.

EXAMPLE 1

This example describes the separation of a mixture of three N-(2,4-dinitrophenyl)amino acids using pH-zone-refining countercurrent chromatography.

Separation of three amino acid derivatives was carried out using a commercial high-speed centrifugal countercurrent chromatograph. The apparatus held a multilayer-coil separation column and a counterweight symmetrically on the rotary frame at a distance of 10 cm from the centrifugal axis of the centrifuge. The column consisted of approximately 165 m×1.6 mm I.D. polytetrafluoroethylene (PTFE) tubing with a total capacity of approximately 330 mL. The multi-layer coil separation column used for most of the semi-preparative and preparative scale separations was constructed by Dr. Y. Ito and typically consisted of 16 coiled layers. Similar columns are commercially available from Shimadzu, Kyoto, Japan and from P.C. Inc., Potomac, Md., USA. The column holder underwent a particular mode of planetary motion: one rotation about its own axis per one revolution around the central axis of the centrifuge, both in the same direction. The revolution speed was regulated with a speed controller.

The solvent system used was composed of a mixture of methyl tert-butyl ether/acetonitrile/water (4:1:5 by volume). This solvent mixture was equilibrated in a separatory funnel at room temperature and the two phases were separated. The upper organic phase was acidified with trifluoroacetic acid (0.04% volume/volume) and used as the stationary phase. A sample solution of a mixture of DNP-L-aspartic acid, DNP-L-alanine, and DNP-L-leucine in 3 mL each of the stationary phase and the neutral lower phase was prepared. The remaining portion of the lower phase was made basic with concentrated ammonium hydroxide (0.1% volume/volume) to pH 10.8 and was used as the mobile phase.

The separation column was first entirely filled with the upper, organic (stationary) phase and the sample solution was injected through a sample port. The column was rotated at 800 rpm while the mobile phase was pumped into the column at a flow-rate of 3 mL/min using a metering pump (Milton Roy minipump; LDC Analytical, Riviera Beach, Fla. USA). Three mL fractions were collected and the absorbance of each was measured using an LKB Uvicord S (LKB Instruments, Stockhol, Sweden) at 206 nm. Additionally, the pH of each fraction was determined by a portable pH meter (Accumet Portable Laboratory, Fischer Scientific, Pittsburgh, Pa., USA) or a model 25 pH meter (Radiometer, Copenhagen, Denmark). The results are shown in FIG. 1.

As FIG. 1 illustrates, the initial fractions collected contain only small amounts of TFA which is undetected by UV spectroscopy (at 206 nm) but which generates a gradual decrease in the pH of the eluant. The TFA which elutes is a result of an equilibrium which is established between the acidified organic stationary phase and the basified aqueous mobile phase. After TFA elutes, the DNP-amino acids elute as three abutting rectangular peaks (absorbance plateaus). Each of the fractions for a particular rectangular peak contain approximately equivalent concentrations of the DNP-amino acid, as evidenced by the absorbance plateau, and each exhibits a pH representative of each DNP-amino acid. The continuous absorbance (solid line), and the pH (- - -) and partition coefficient for the solutes (• • •) of each fraction are shown. The partition coefficients for each fraction were measured in a standard two-phase solvent system composed of chloroform/acetic acid/0.1M hydrochloric acid (2:2:1 by volume). The graph of the partition coefficient of each fraction had three plateaus that coincided with the absorbance plateaus. The partition coefficients at these three plateaus are equal to the partition coefficients of the pure DNP-amino acids. Thus the plateaus are the tops of three abutting rectangular peaks, each containing a single DNP-amino acid. The sharp transitions in absorbance, partition coefficient and pH between the peaks show that overlap is minimal.

EXAMPLE 2

Figure 2:
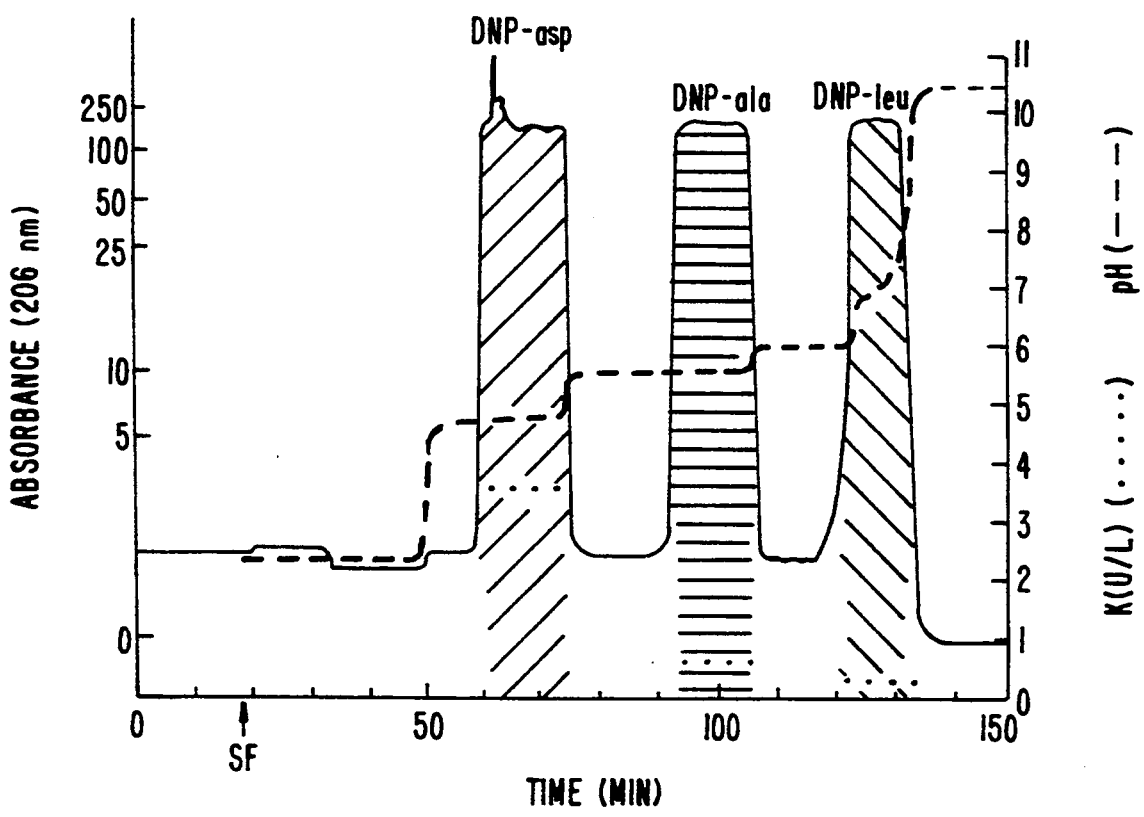
FIG. 2 shows the separations of the three amino acids of FIG. 1 with added amounts of acetic, propionic and butyric acids (0.4% each, volume/volume) as described in Example 2.

This example illustrates the separation of a mixture of three DNP-amino acids as in Example 1, to which acetic, propionic and butyric acids (0.4% each, volume/volume) were added. The apparatus and conditions used were identical to those of Example 1. A chromatogram showing the elution results is shown in FIG. 2. The fractions collected after the solvent front initially contain undetected TFA, as equilibrium is established between the phases. After TFA elutes, the DNP-amino acids elute as three rectangular peaks, preceded by undetected acetic acid (evidenced by the pH increase) and separated by absorbance valleys corresponding to undetected propionic and butyric acids (but evidenced by pH increases). The continuous absorbance (solid line), and the pH (- - -) and partition coefficient (• • •) of each fraction are shown. The partition coefficients for each fraction were measured in a standard two-phase solvent system composed of chloroform/acetic acid/0.1M hydrochloric acid (2:2:1 by volume). As in Example 1, the partition coefficient plateau regions correspond to the absorbance plateau regions and provide a further demonstration of the purity and constant concentration within each of the rectangular peaks.

EXAMPLE 3

This example illustrates the separation and recovery of the major components of the dye D&C Orange No. 5 by pH-zone-refining CCC. D&C Orange No. 5 is identified as a mixture containing mainly three hydroxyxanthene dyes: 50–60% of 4',5'-dibromofluorescein (I); 30–40% of 2',4',5'-tribromofluorescein (II); and ≦10% of 2',4',5',7'-tetrabromofluorescein (III) (*Code of Federal Regulations*, Title 21, Section 74.1255, U.S. Government Printing Office, Washington, D.C., 1991).

Separation of the components of D&C Orange No. 5 using pH-zone-refining CCC was carried out using the apparatus and column of Example 1. The solvent system used to separate the components consisted of diethyl ether/acetonitrile/0.01M aqueous ammonium acetate adjusted to pH 9 with ammonium hydroxide (4:1:5 by volume). The solvent system was equilibrated and the two resulting phases were separated. A sample mixture was prepared by partitioning 5 g of certified D&C Orange No. 5 between 40 mL each of the upper and lower phases. The upper organic phase was used as the stationary phase. The lower aqueous phase was used as the mobile phase without further addition of base.

The separation column was filled with the stationary phase. Trifluoroacetic acid (200 μL) was added to the sample solution. Following the addition of the acid, a portion of the dye precipitated. The resulting suspension was sonicated for approximately 1 minute and then injected into the column. The column was rotated at 800 rpm while the mobile phase was pumped into the column at a flow rate of 3 mL/min. The eluate was collected in 3-mL fractions and the absorbance of each was monitored using an LKB Uvicord S at 254 nm. In addition, the pH of each fraction was recorded. The results are shown in FIG. 3A.

The chromatogram has a broad rectangular shape comparable to the chromatogram of the DNP-amino acids (FIG. 1). The three broad absorbance plateaus (solid line) correspond to the three pH-plateaus (- - -). Each plateau represents elution of a pure compound as illustrated by the associated reverse phase-HPLC chromatograms of the combined fractions from the three hatched regions (FIGS. 3B, 3C and 3D). Each pH transition on the dashed line corresponds to an absorbance transition. Impurities were concentrated in the few fractions either preceding or between the constant pH and absorbance zones (HPLC analysis not shown). The sequence of elution of the three main components in this sample is in the order of their increasing $pK_{a2}$: Compound III < Compound II < Compound I. The acid dissociation constants for the carboxylic acid moieties ($pK_{a1}$) and the phenolic moieties ($pK_{a2}$) have been determined for the compounds as follows. For 2',4',5',7'-tetrabromofluorescein (III), $pK_{a1} = 3.25$ and $pK_{a2} = 3.80$ (P. Levillain and D. Fompeydie, *Anal. Chem.*, 57:2561 (1985)). For 2',4',5'-tribromofluorescein (II), $pK_{a1} = 3.64$ and $pK_{a2} = 4.34$, and for 4',5'-dibromofluorescein (I), $pK_{a1} = 3.55$ and $pK_{a2} = 4.8$ (D. Fompeydie, Faculte des Sciences Pharmaceutique et Biologiques, Paris, France, personal communication).

Recovery of each of the components of the dye mixture was calculated as a percentage of the amount initially present in the dye. The dyes were isolated in the lactone form by combining the fractions containing a pure solute and concentrating the mixture to a volume of about 1 mL on a rotary evaporator at 25–30 mmHg at a temperature of about 50° C. The residue was acidified with 10–15 mL of 10% HCl and the precipitated lactones were extracted into ethyl acetate. The organic layer was washed (2×10 mL water) and dried (anhydrous Na₂SO₄), and the solvent was evaporated. Results are shown in Table I.

TABLE I pH-Zone-Refining Countercurrent Chromatography of D&C Orange No. 5[a]

| Sample size (mg) | Recovery (%)[b] | | |
|---|---|---|---|
| | I | II | III |
| 350 | 77.2 | 87.3 | 42 |
| 5000 | 82.0 | 90.3 | 77 |

[a]FDA certified batch.
[b]Isolated as lactones, see A. Weisz, et al., J. Chromatogr., 607:47-53 (1992), and identified by chemical ionization mass spectrometry and by ¹H-nuclear magnetic resonance.

Figure 4:
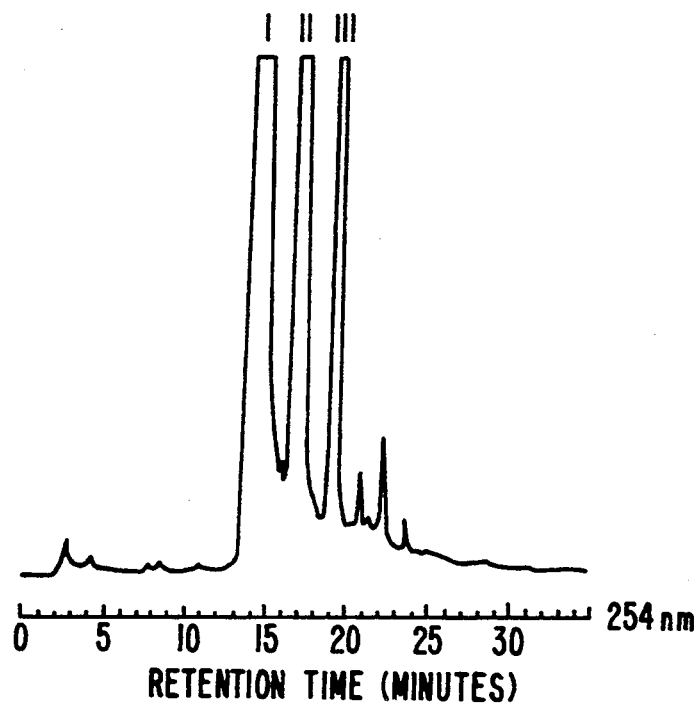
FIG. 4 shows an analytical RP-HPLC separation of the D&C Orange No. 5 sample used for the pH-zone-refining CCC shown in FIG. 3.

A chromatogram of a reverse-phase HPLC analysis of the D&C Orange No. 5 is shown in FIG. 4. Chromatography was carried out on a system consisting of a Model 8800 ternary pump, Model 8500 dynamic mixer, Model 8780 autosampler and Model 4270 integrator (all from Spectra-Physics, San Jose, Calif., USA), and a Model 490 dual-wavelength UV-VIS detector set at 254 nm (Waters Assoc., Milford, Mass., USA). The autosampler was equipped with a Model 7010 injector (Rheodyne, Cotati, Calif., USA) with a 200-μL sample loop. A Hypersil MOS-1 RPC-8 column (5 μm particle size, 250×4.6 mm I.D., Keystone Scientific, Bellefonte, Pa., USA) was used. Eluants were 0.1M aqueous NH₄OAc and methanol. The column was eluted using consecutive linear gradients of 25 to 90% methanol in 25 min, 90 to 100% methanol in 5 min, and 100% methanol for 5 min. An injection volume of 20 μL was used with a full scale absorbance response of 0.128 and a flow-rate of 1 mL/min.

In each of the following examples the dyes were isolated as lactones (described above) and RP-HPLC was conducted using the above method.

pH-zone-refining CCC separations of 0.35, 1 and 5 g of D&C Orange No. 5 resulted in proportionate increases in peak width and pH-plateau length. The small degree of overlap between the peaks was maintained.

EXAMPLE 4

Figure 5:
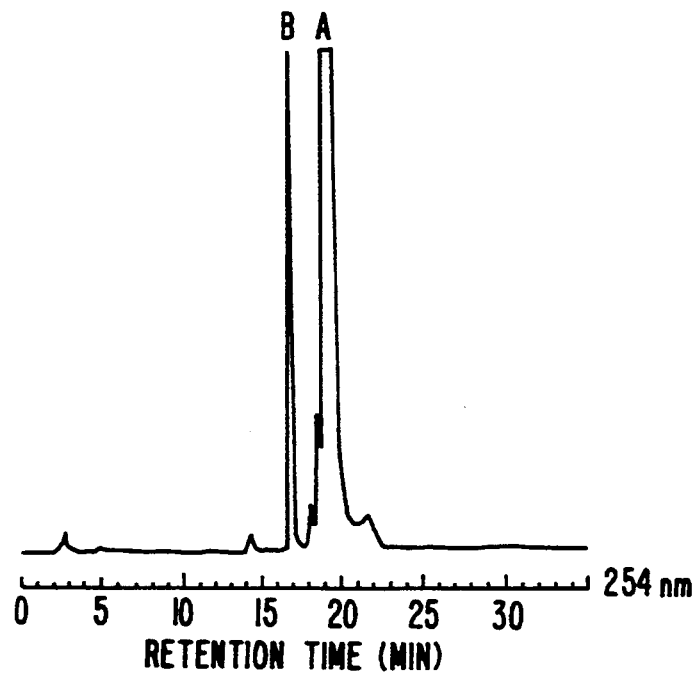
FIG. 5 shows an analytical RP-HPLC separation of the D&C Red No. 22 sample used for the pH-zone-refining CCC shown in FIG. 6.

This example illustrates the separation of 2′,4′,5′,7′-tetrabromofluorescein from the color additive D&C Red No. 22 (Eosin Y). D&C Red No. 22 (Color Index No. 45380) is a U.S.-certified color additive used in drugs and cosmetics. It is a mixture of tri- and tetrabromofluorescein dyes having ≦25% sum of disodium salts of tribromofluoresceins and ≧72% disodium salt of 2′,4′,5′,7′-tetrabromofluorescein. The total dye content for D&C Red No. 22 is approximately 90%. Eosin Y is a similar mixture having a dye content of approximately 80% and it finds use as an important biological stain. FIG. 5 shows the RP-HPLC chromatogram from the sample used in this separation.

The separation of 5 g of D&C Red No. 22 was carried out using the apparatus as described in Example 1. The solvent system consisting of ether/acetonitrile/0.01M ammonium acetate (4:1:5 by volume, 1000 mL total volume) was equilibrated and the two phases were separated. The lower phase was adjusted to pH 8.35 by adding ammonium hydroxide. The upper phase was acidified with 800 μL of TFA (pH=1.86). It was found advantageous to acidify the upper phase rather than the sample solution as in Example 3. This avoided precipitation of the dye from solution and simplified injection of the sample solution into the column. The sample solution was prepared by partitioning 5 g of D&C Red No. 22 in a mixture of the upper and lower phases (15 mL each). Injection of the sample into the column and the subsequent separation of the components was carried out as described in Example 3.

Figure 6A:
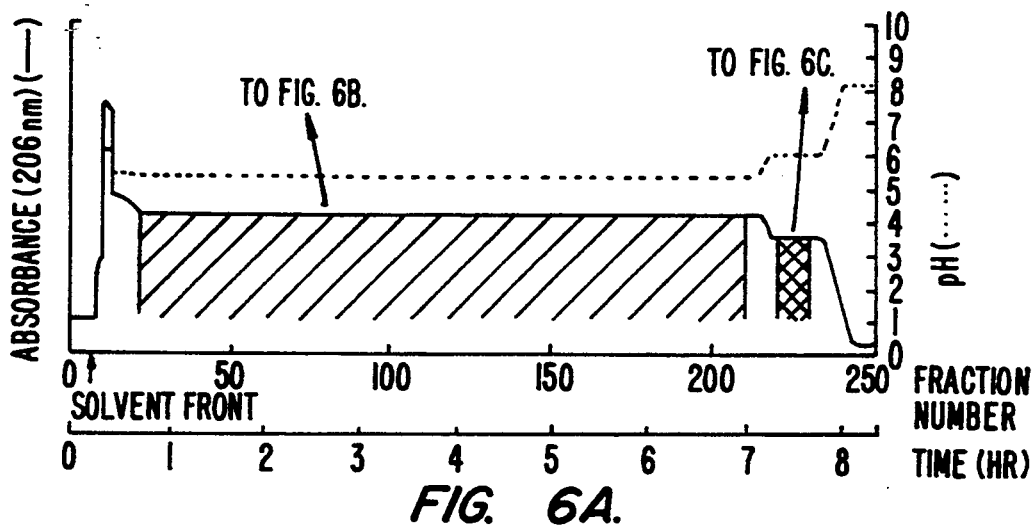
FIG. 6A shows the trace from the collected fractions following pH-zone-refining CCC.
Figure 6B:
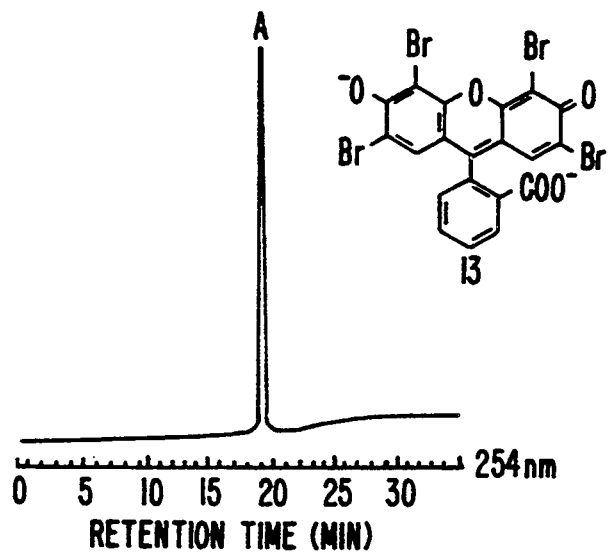
FIGS. 6B and 6C show RP-HPLC chromatograms from the combined fractions corresponding to the separated components of D&C Red No. 22 (Example 4).
Figure 6C:
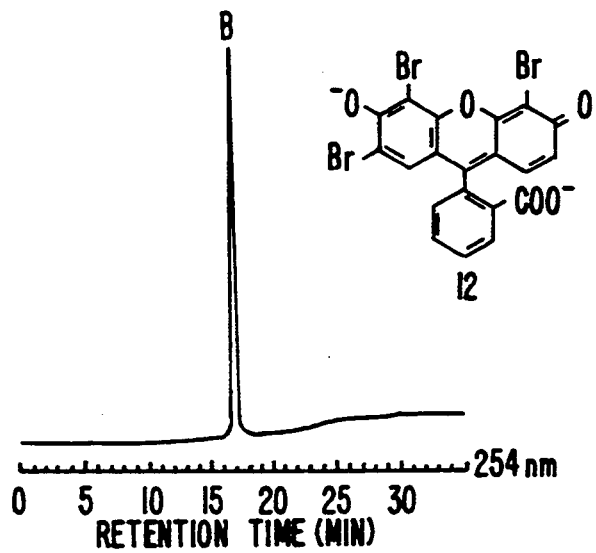

The resulting chromatogram, shown in FIG. 6, has a broad rectangular shape. The two broad absorbance plateaus correspond to the two pH plateaus. Fractions 20–210 contained the main component as a concentrated solution. 2′,4′,5′,7′-Tetrabromofluorescein (1.46 ) was isolated in the lactone form as described in Example 3 and identified by chemical ionization mass spectroscopy (CIMS) and proton nuclear magnetic resonance spectroscopy (¹H NMR). Fractions in the second plateau region provided 31 mg of 2′,4′,5′-tribromofluorescein which was also identified by CIMS and ¹H NMR. Earlier fractions (fractions 10–15) contained the main component which eluted as a suspension. Reverse phase HPLC analyses of these fractions showed a number of impurities.

EXAMPLE 5

Figure 7:
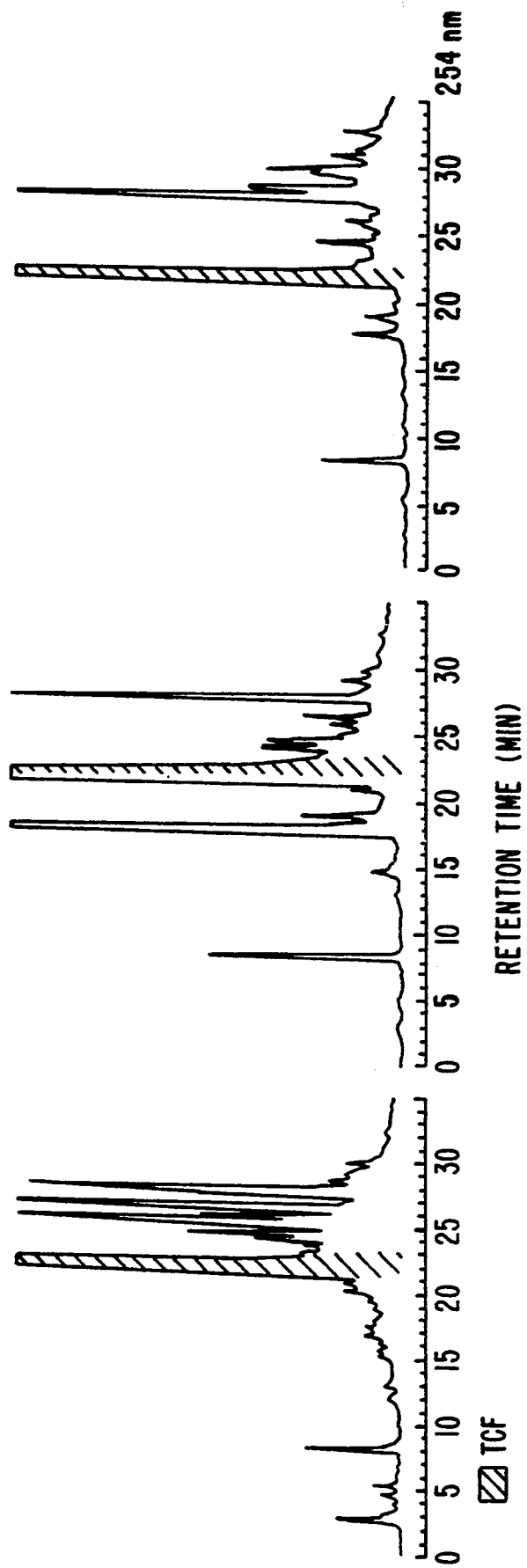
FIG. 7 shows analytical RP-HPLC chromatograms of batches of 4,5,6,7-tetrachlorofluorescein (TCF) obtained from three different distributors.

This example illustrates the purification of a commercial sample of 4,5,6,7-tetrachlorofluorescein (TCF) using pH-zone-refining CCC. TCF is a dye of the hydroxyxanthene class and is used for the preparation of more highly halogenated dyes such as Phloxine B, Rose Bengal, and 2′,4′,5′,7′-tetrabromo-4,5,6,7-tetrachlorofluorescein. These dyes are used as biological stains and are also the main components of U.S.-certified color additives which are used in drugs and cosmetics. TCF from commercial sources contains a number of contaminants. FIG. 7 shows reverse phase HPLC chromatograms from several batches of TCF obtained from various distributors. As the chromatograms indicate, the specific contaminants vary between samples. The contaminants of TCF can be carried over in the manufacturing process of the more highly halogenated dyes and can significantly affect the proposed uses for those dyes.

Purification of 4,5,6,7-tetrachlorofluorescein was carried out using the apparatus as described in Example 1. The two-phase solvent system used for this separation was composed of diethyl ether/acetonitrile/(0.01M ammonium acetate adjusted to pH 9 with ammonium hydroxide) (4:1:5 by volume). The solvent system was equilibrated and the two phases were separated shortly before use. The sample mixture was prepared by partitioning 350 mg of commercial TCF between 5.5 mL of each of the upper and lower phases. Trifluoroacetic acid (200 μL) was added to the sample solution. Injection of the sample solution into the column and the subsequent purification of 4,5,6,7-tetrachlorofluorescein by pH-zone-refining CCC was as described in Example 3.

Figure 8:
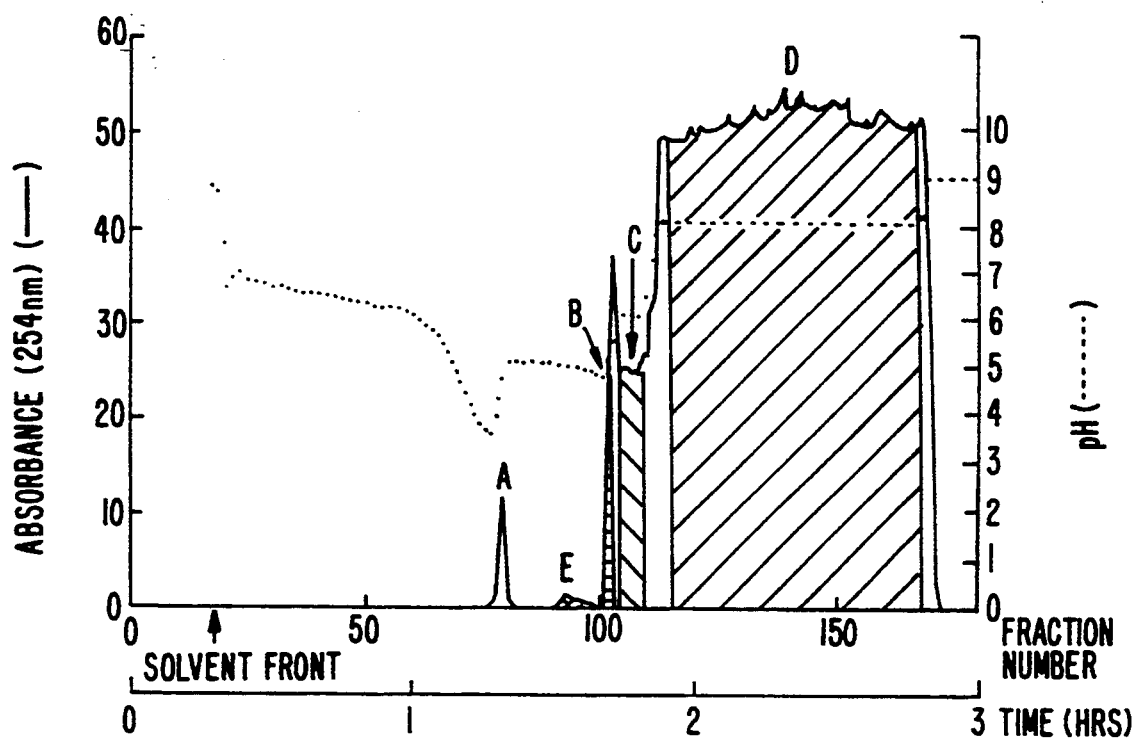
FIG. 8 shows the separation of a 350 mg portion of commercial TCF by pH-zone-refining CCC.
Figure 9:
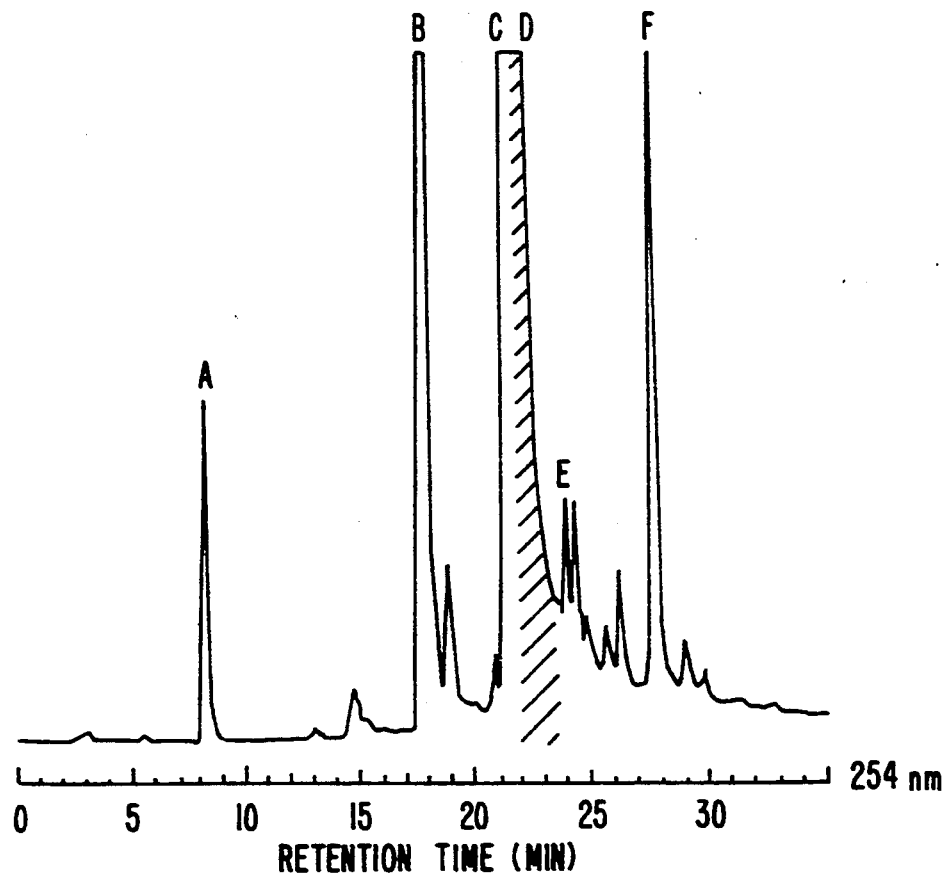
FIG. 9 shows the analytical RP-HPLC chromatogram of the sample of TCF used for the pH-zone-refining CCC separation in FIG. 8 (described in Example 5).
Figure 10A:
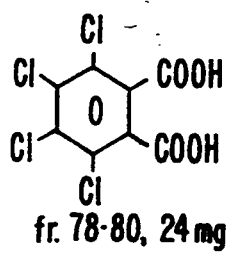
FIG. 10 provides the structures and amounts of the components isolated in the various fractions from the separation of 350 mg of TCF (Example 5).
Figure 10B:
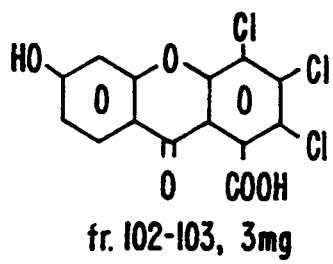
Figure 10C:
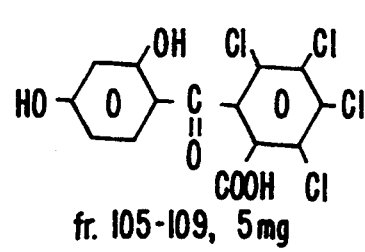
Figure 10D:
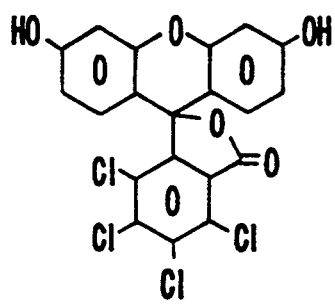
Figure 10E:
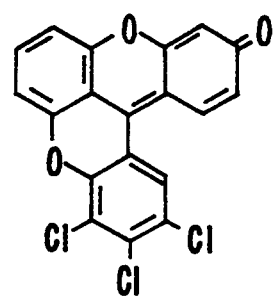

FIG. 8 shows the resulting CCC chromatogram having five absorbance peaks (labeled A-E). Each of the absorbance peaks contained a single component that corresponded to one of the reverse phase HPLC peaks in FIG. 9. The components were isolated and identified by two or more of the following methods: CIMS, ¹H NMR, high-resolution MS and RP-HPLC. FIG. 10 shows the structures of the components which were isolated, the fractions collected and the amounts of each. The letter labels correspond to the hatched areas and peaks in FIGS. 8 and 9, respectively.

pH-Zone-refining CCC separation of a 2 g portion of commercial TCF (the same batch that was used above) was also carried out. A less polar solvent system composed of methyl t-butyl ether/acetonitrile/water (4:1:5 by volume, total volume of 1000 mL) was used. The pH of the lower phase was adjusted to 10.63 with ammonium hydroxide. The upper phase was acidified with 200 μL of TFA (pH=2.52). The sample was prepared by suspending 2 g of TCF in 100 mL of the acidified upper phase and injected into the column without prior filtration. The resulting pH-zone-refining CCC chromatogram showed proportionate increases in peak width and pH plateaus and in good recoveries of the main compound.

EXAMPLE 6

This example illustrates the separation of 2',4',5',7'-tetrabromo-4,5,6,7-tetrachlorofluorescein from the color additive D&C Red No. 28 (Phloxine B).

Figure 11:
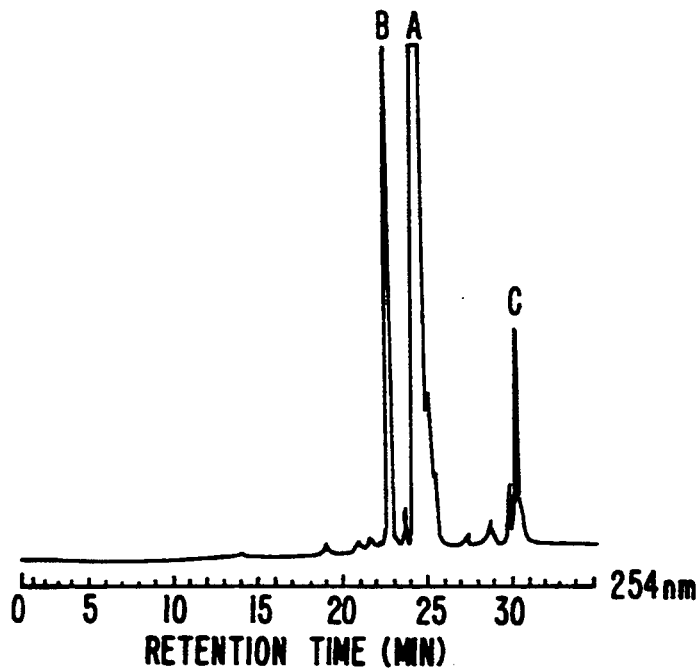
FIG. 11 shows an analytical RP-HPLC chromatogram of the sample of D&C Red No. 28 used in the 3 g separation described in Example 6.

D&C Red No. 28 is a U.S.-certified color additive used in drugs and cosmetics. It is identified as principally the disodium salt of 2',4',5',7'-tetrabromo-4,5,6,7-tetrachlorofluorescein and may contain lower halogenated subsidiary colors (≦4%) and the ethyl ester of 2',4',5',7'-tetrabromo-4,5,6,7-tetrachlorofluorescein (≦2%). FIG. 11 shows a RP-HPLC chromatogram of a certified lot of D&C Red No. 28. Using a semipreparative CCC column and conditions for pH-zone-refining CCC, multigram quantities of 2',4',5',7'-tetrabromo-4,5,6,7-tetrachlorofluorescein can be isolated from the commercial dye. The apparatus used for this separation is identical to the apparatus used in Example 1.

Figure 12A:
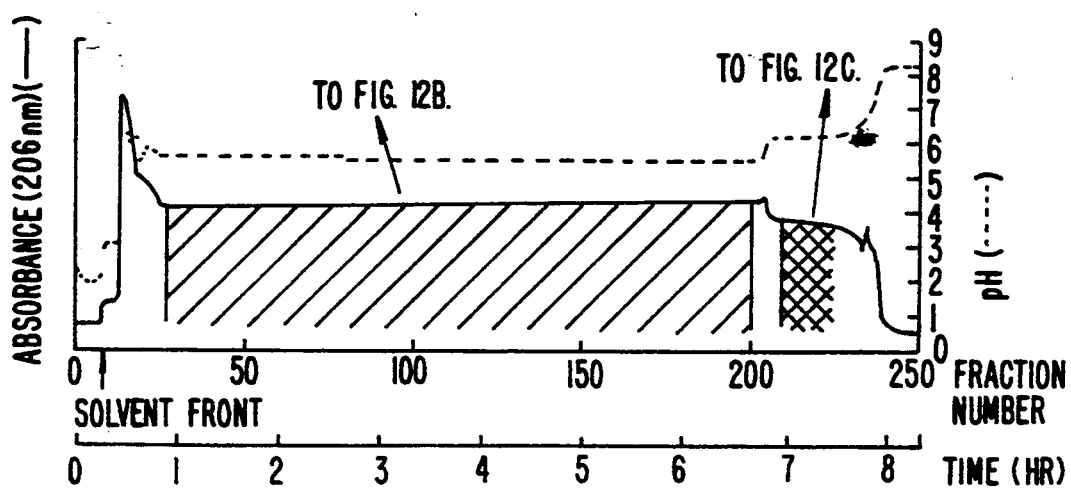
FIG. 12A shows the trace from the collected fractions following pH-zone-refining CCC.
Figure 12B:
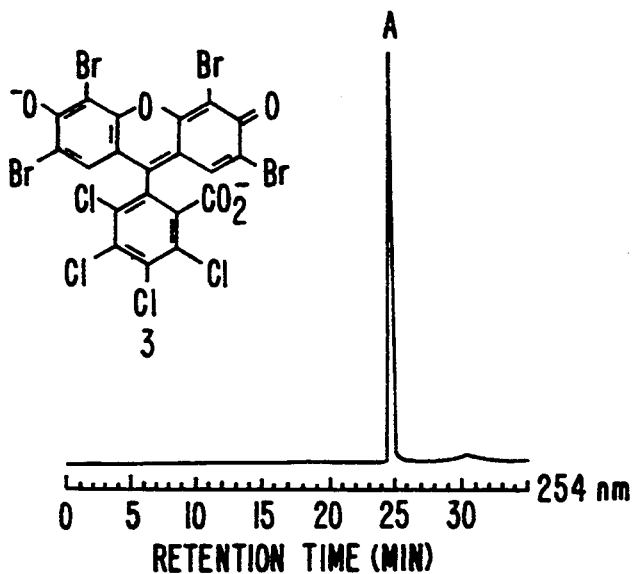
FIGS. 12B and 12C show RP-HPLC chromatograms of the combined fractions corresponding to the separated components of D&C Red No. 28 (Example 6).
Figure 12C:
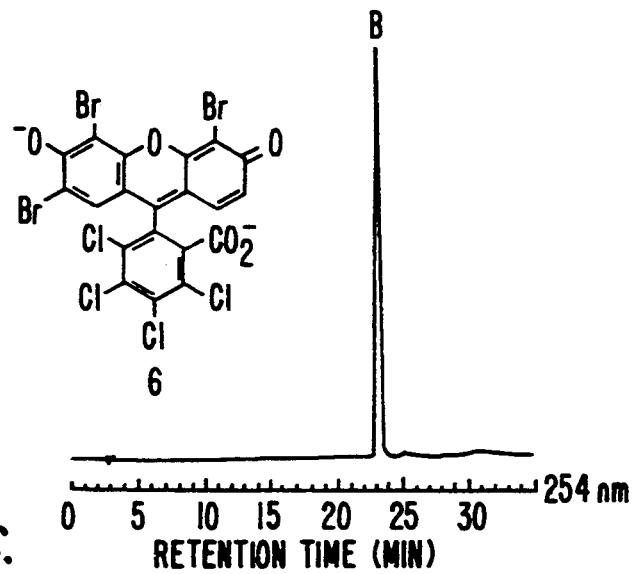

The two-phase solvent system used consisted of diethyl ether/acetonitrile/0.01M ammonium acetate (4:1:5 by volume). The pH of the lower phase was adjusted to 8.12 by addition of ammonium hydroxide. The sample mixture was prepared by partitioning 3 g of dye in a solvent consisting of 20 mL of the lower phase and 10 mL of the upper phase. TFA (600 μL) was added to 500 mL of the upper phase. The sample mixture was loaded into the column and eluted as described for Example 3. The resulting chromatogram (FIG. 12) has a broad rectangular shape having two absorbance plateaus which correspond to the two pH plateaus. The fractions corresponding to the horizontal plateaus (fractions 27–200 and fractions 209–225) contained pure compounds. These compounds (isolated in lactone form) were identified by CIMS and ¹H NMR as 2',4',5',7'-tetrabromo-4,5,6,7-tetrachlorofluorescein (yield: 1.07 g) and 2',4',5'-tribromo-4,5,6,7-tetrachlorofluorescein (yield: 61 mg). Earlier fractions contained the main component as a suspension, slightly contaminated with other impurities. The less polar component of the mixture that corresponds to peak C in FIG. 11 remained in the stationary phase in the column.

Figure 13:
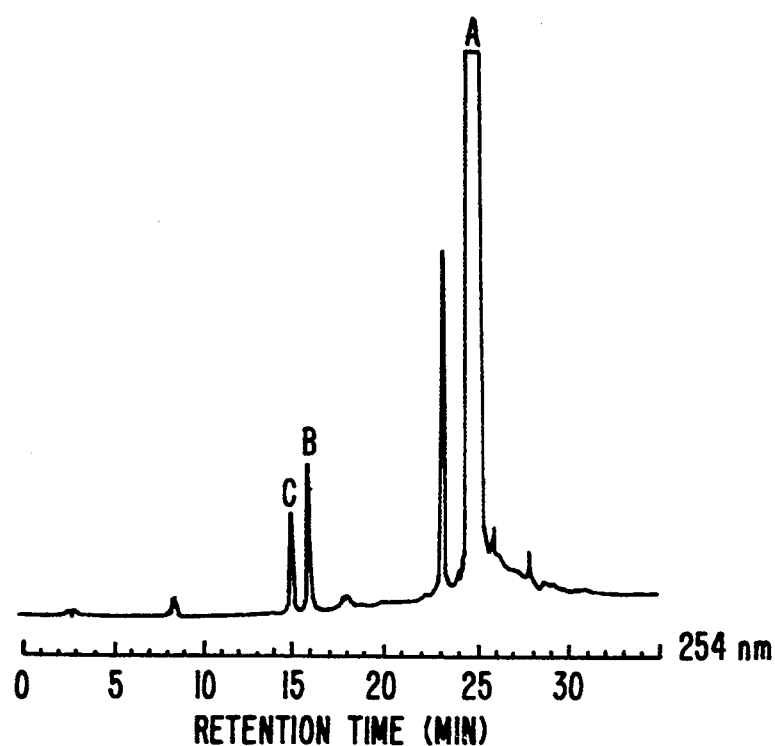
FIG. 13 shows an analytical RP-HPLC chromatogram of the sample of D&C Red No. 28 used in the 6 g separation described in Example 6.
Figure 14A:
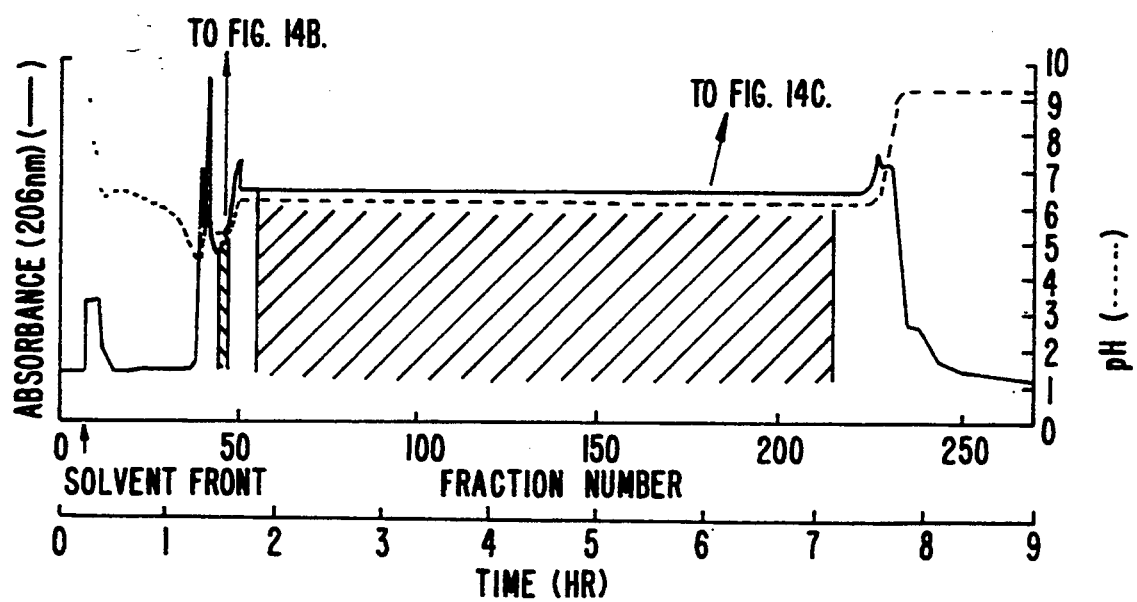
FIG. 14A shows the trace from the collected fractions following pH-zone-refining CCC.
Figure 14B:
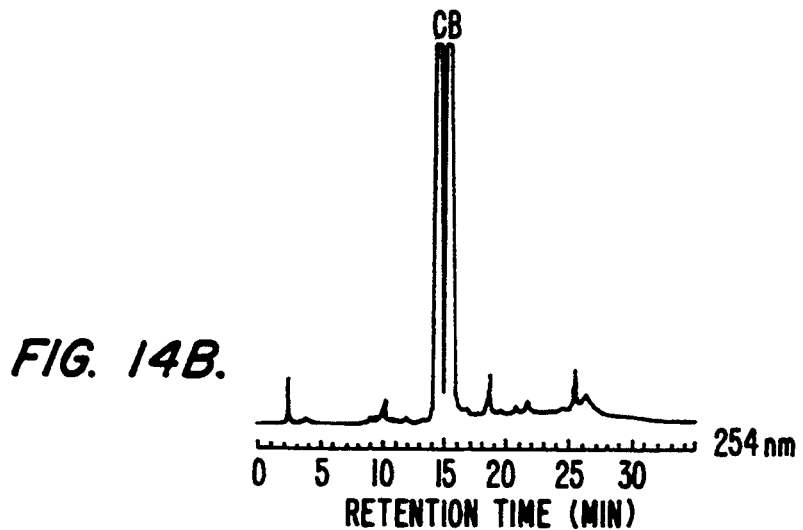
FIGS. 14B and 14C show RP-HPLC chromatograms of the combined fractions corresponding to the separated components of D&C Red No. 28.
Figure 14C:
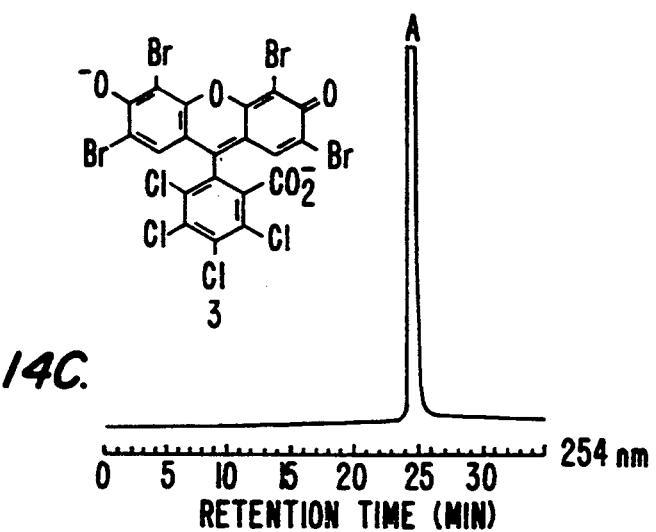

In larger separations of D&C Red No. 28, it was found to be more advantageous to add the retaining acid (TFA) to the sample solution. Thus, a 6 g sample from a different batch of D&C Red No. 28 was separated using the above procedure with the following modifications. After the two phases of the solvent system were separated, the lower phase was adjusted to pH 9.21 with ammonium hydroxide. The 6 g sample was dissolved in 50 mL of solvent consisting of 20 mL of the lower phase and 30 mL of the upper phase. TFA (1.2 mL) was then added to the sample solution. The sample solution was loaded onto the column and eluted as above. FIG. 13 shows an analytical RP-HPLC chromatogram of the 6 g sample prior to pH-zone-refining CCC. FIG. 14 shows the resultant chromatogram from pH-zone-refining CCC. The recovery of the main component (4.06 g in the lactone form) was improved because no unseparated suspension eluted in the first fractions. The two components corresponding to peaks B and C in FIG. 13 eluted in a very concentrated form in earlier fractions.

EXAMPLE 7

This example illustrates the separation of three iodinated fluorescein dyes from the color additive FD&C Red No. 3 (Erythrosine). FD&C Red No. 3 (Color Index No. 45430) is a U.S.-certified color additive used in food, drugs and cosmetics. Under the name Erythrosine, this dye is used as a biological stain. The dye is identified as a mixture containing principally the disodium salt of 2',4',5',7'-tetraiodofluorescein. Other lower iodinated fluoresceins total not more than 9%.

Figure 15:
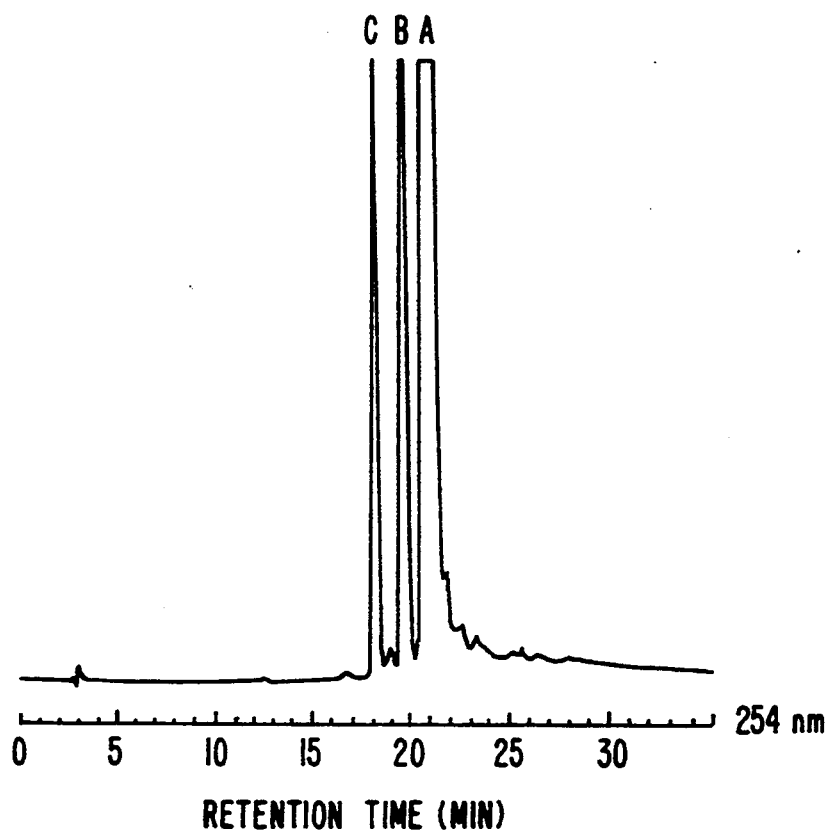
FIG. 15 shows an analytical RP-HPLC chromatogram of the sample of FD&C Red No. 3 used in Example 7.

A separation of a 3 g portion of color additive FD&C Red No. 3 was carried out by pH-zone-refining CCC with the apparatus and general procedure described in Example 1. The two-phase solvent system used consisted of diethyl ether/acetonitrile/0.01 M ammonium acetate (4:1:5 by volume). The solvents were equilibrated and the phases were separated. The pH of the lower phase was adjusted to 7.53 by the addition of ammonium hydroxide. The upper, stationary phase (500 mL) was acidified with trifluoroacetic acid (400 μL). The sample solution was prepared by partitioning 3 g of dye in a solvent consisting of 20 mL of the lower phase and 20 mL of the unacidified upper phase. FIG. 15 shows an RP-HPLC chromatogram of the sample before separation. The sample solution was injected into the column and eluted as described in Example 3.

Figure 16A:
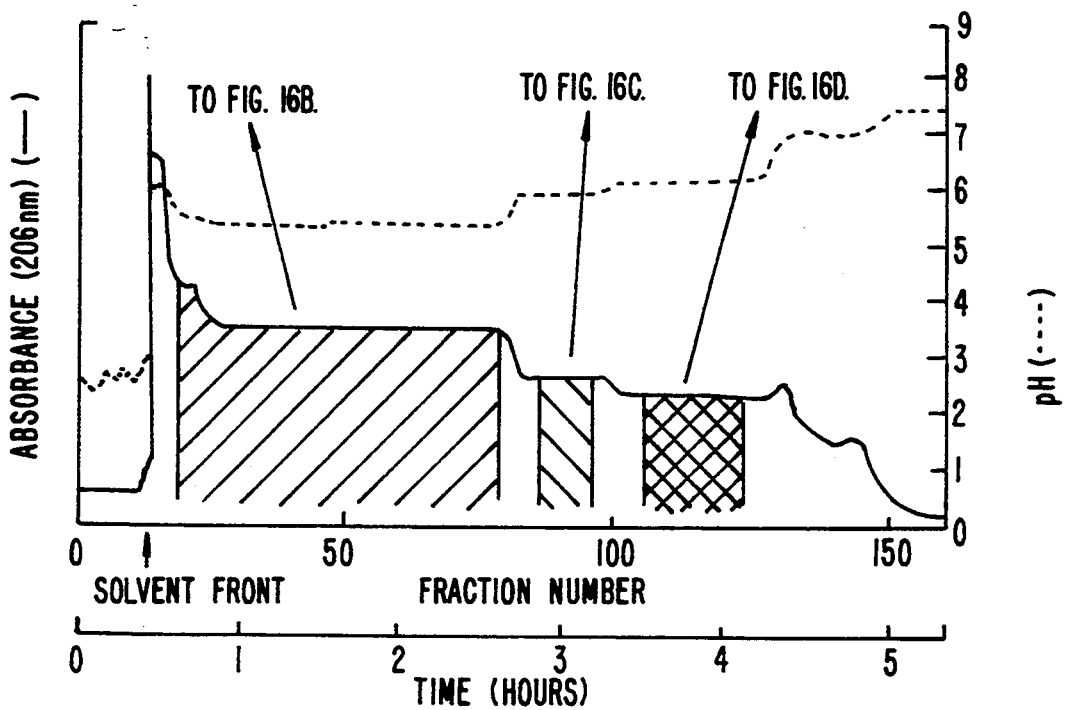
FIG. 16A shows the trace from the collected fractions following pH-zone-refining CCC.
Figures 16B, 16C:
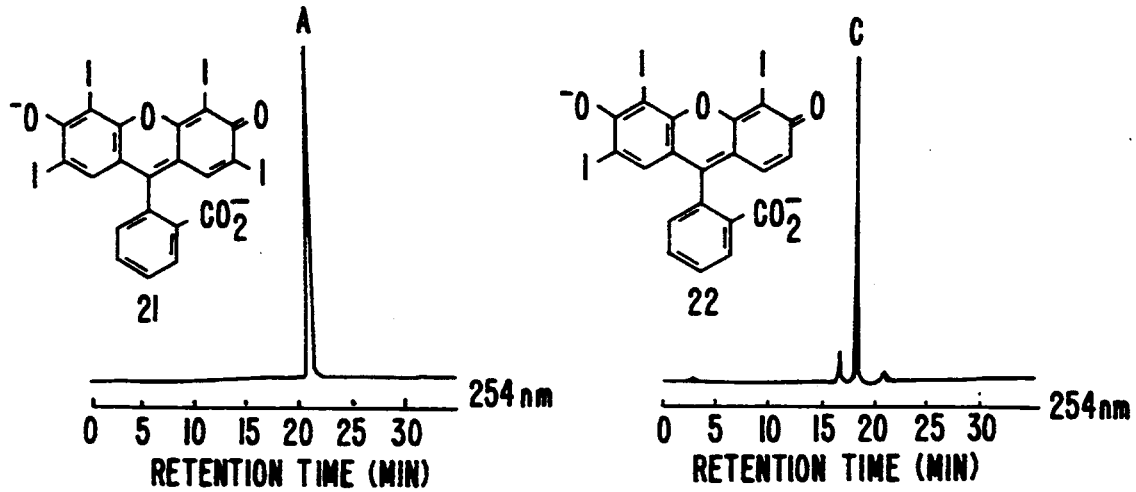
FIGS. 16B, 16C and 16D show RP-HPLC chromatograms of the combined fractions corresponding to the separated components of FD&C Red No. 3.
Figure 16D:
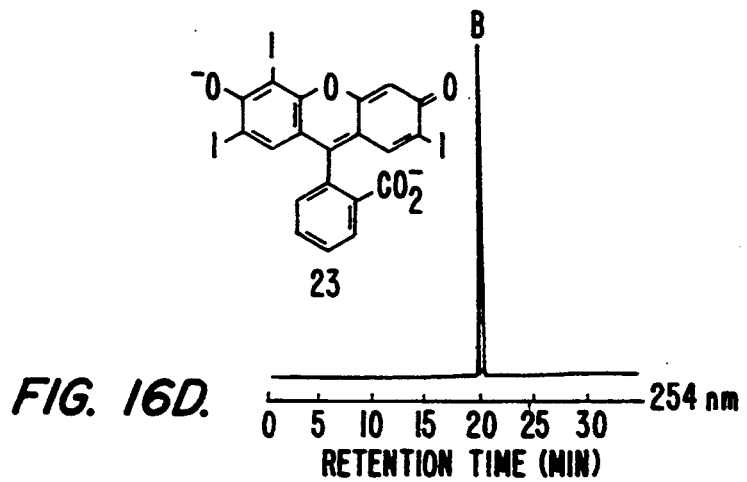

FIG. 16 shows the resulting CCC chromatogram and the analytical RP-HPLC chromatograms corresponding to the separated components. As in the previous separations in which the retaining acid (TFA) was added to the stationary phase, the response before the first absorbance plateau decreases in intensity due to the presence of a suspension. The suspension that eluted in these first fractions contained the main component slightly contaminated with other impurities. The fractions corresponding to the horizontal plateaus contained single compounds that were isolated in the lactone form and characterized by CIMS and ¹H NMR. The separation resulted in the recovery of 400 mg of 2',4',5',7'-tetraiodofluorescein (peak A in FIGS. 15 and 16) and of two positional isomers of lower-iodinated subsidiary colors, 2',4',5'-triiodofluorescein (22 mg, peak C in FIGS. 15 and 16) and 2',4',7'-triiodofluorescein (52 mg, peak B in FIGS. 15 and 16).

EXAMPLE 8

This example illustrates the separation of 4',5'-diiodo- and 2',4',5'-triiodofluorescein from the color additive D&C Orange No. 10.

Figure 17:
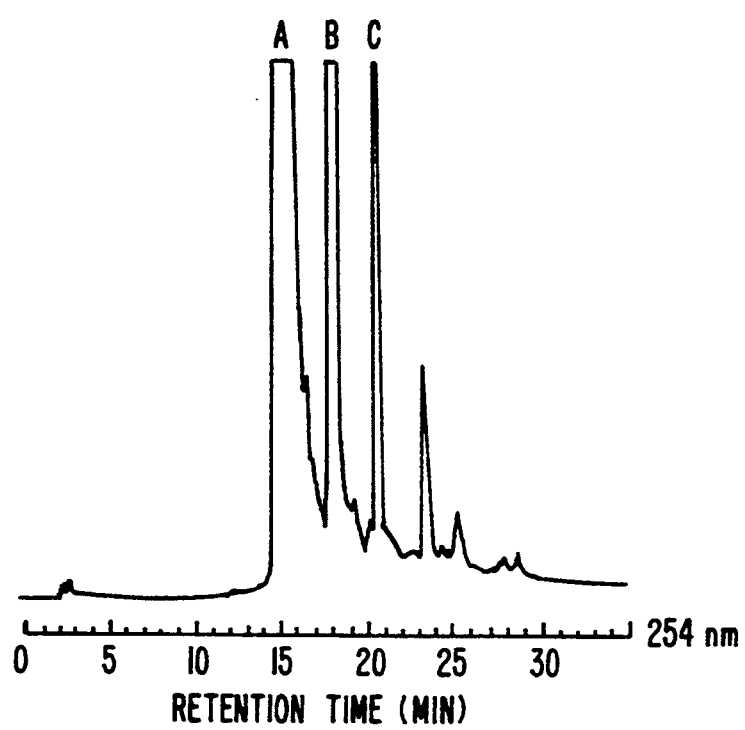
FIG. 17 shows an analytical RP-HPLC chromatogram of the sample of D&C Orange No. 10 used in Example 8.

D&C Orange No. 10 (Color Index No. 45425:1) is a U.S.-certified color additive used in drugs and cosmetics. It is identified as a mixture containing principally three hydroxyxanthene dyes: 4',5'-diiodofluorescein (60–95%), 2',4',5'-triiodofluorescein (≦35%), and 2',4',5',7'-tetraiodofluorescein (≦10%). FIG. 17 shows the analytical RP-HPLC chromatogram of the commercial sample used in this separation.

A separation of a 350 mg portion of color additive D&C Orange No. 10 was carried out by pH-zone-refining CCC with the apparatus and general procedure described in Example 1. The two-phase solvent system used consisted of diethyl ether/acetonitrile/0.01M ammonium acetate (4:1:5 by volume). The solvents were equilibrated and the phases were separated. The pH of the lower phase was adjusted to 9.16 by the addition of ammonium hydroxide. The sample mixture was prepared by partitioning 350 mg of D&C Orange No. 10 between 5 mL of each of the upper and lower phases. The retaining acid (TFA, 300 μL) was added to the sample mixture. The resulting suspension was injected into the column without filtering and eluted with the basic aqueous mobile phase.

FIG. 18 shows the resulting CCC chromatogram and the analytical RP-HPLC chromatograms corresponding to the separated components. The CCC chromatogram has a broad rectangularly shaped absorbance peak. Monitoring the pH of the eluted fractions revealed a short and a long pH plateau corresponding to the separated compounds. The compounds were isolated in their lactone forms and identified by CIMS and $^1$H NMR. This separation resulted in the recovery of 2',4', 5'-triiodofluorescein (20 mg, peak B in FIGS. 17 and 18, contaminated with trace amounts of mono- and diiodofluorescein) and 4',5'-diiodofluorescein (244 mg, peak A in FIGS. 17 and 18).

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A method for separating a quantity of an acidic compound from other compounds in a mixture using pH-zone-refining countercurrent chromatography, comprising:
   (a) adding acid to a first liquid phase of two pre-equilibrated immiscible liquid phases and charging a countercurrent chromatographic centrifuge column with said first liquid phase, thereby producing a countercurrent chromatographic centrifuge column charged with said thus acidified first liquid phase;
   (2) adding base to a second liquid phase of said two pre-equilibrated immiscible liquid phases to form a basic mobile phase;
   (3) introducing said mixture into said countercurrent chromatographic centrifuge column thus charged with said acidified first liquid phase; and
   (4) passing said basic mobile phase through said countercurrent chromatographic centrifuge column thus charged with said mixture and said acidified first liquid phase, to elute said acidic compound from said countercurrent chromatographic centrifuge column.

2. The method in accordance with claim 1 wherein said first liquid phase is an organic phase.

3. The method in accordance with claim 1 wherein said second liquid phase is an aqueous phase.

4. The method in accordance with claim 1 wherein said first liquid phase is an organic phase and said second liquid phase is an aqueous phase.

5. The method in accordance with claim 1 wherein said quantity is from 0.01 to 100 grams.

6. The method in accordance with claim 1 wherein said first liquid phase is made acidic with an organic acid selected from the group consisting of acetic acid, trifluoroacetic acid, propionic acid and butanoic acid.

7. The method in accordance with claim 1 wherein said first liquid phase is made acidic with trifluoroacetic acid.

8. The method in accordance with claim 1 wherein said mixture is a suspension.

9. The method in accordance with claim 1 wherein said column is a helical column.

10. A method for separating a quantity of a basic compound from other compounds in a mixture using pH-zone-refining countercurrent chromatography, comprising:
   (a) adding base to a first liquid phase of two pre-equilibrated immiscible liquid phases and charging a countercurrent chromatographic centrifuge column with said first liquid phase, thereby producing a countercurrent chromatographic centrifuge column charged with said thus basified first liquid phase;
   (2) adding acid to a second liquid phase of said two pre-equilibrated immiscible liquid phases to form an acidic mobile phase;
   (3) introducing said mixture into said countercurrent chromatographic centrifuge column thus charged with said basified first liquid phase; and
   (4) passing said acidic mobile phase through said countercurrent chromatographic centrifuge column thus charged with said mixture and said acidified first liquid phase, to elute said acidic compound from said countercurrent chromatographic centrifuge column.

11. The method in accordance with claim 10 wherein said first liquid phase is an organic phase.

12. The method in accordance with claim 10 wherein said second liquid phase is an aqueous phase.

13. The method in accordance with claim 10 wherein said first liquid phase is an organic phase and said second liquid phase is an aqueous phase.

14. The method in accordance with claim 10 wherein said quantity is from 0.01 to 100 grams.

15. The method in accordance with claim 10 wherein said mixture is a suspension.

16. The method in accordance with claim 10 wherein said column is a helical column.

* * * * *